US007785376B1

(12) United States Patent
Chun et al.

(10) Patent No.: US 7,785,376 B1
(45) Date of Patent: Aug. 31, 2010

(54) METHOD FOR BINDING COMPOUNDS TO TEXTILES

(75) Inventors: David T. Chun, Seneca, SC (US); Gary R. Gamble, Seneca, SC (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 115 days.

(21) Appl. No.: 12/273,882

(22) Filed: Nov. 19, 2008

Related U.S. Application Data

(60) Provisional application No. 60/990,720, filed on Nov. 28, 2007.

(51) Int. Cl.
*D06P 1/38* (2006.01)
(52) U.S. Cl. .......................... 8/543; 8/587; 8/916; 8/920
(58) Field of Classification Search .................. 8/543, 8/587, 916, 920
See application file for complete search history.

(56) References Cited

U.S. PATENT DOCUMENTS 4,474,696 A * 10/1984 Takahashi et al. ........... 534/637
4,810,567 A    3/1989 Calcaterra et al.

OTHER PUBLICATIONS

Chun, T.W. et al. "Testing for Antibacterial Properties of Cotton/Flax Denim", Industrial Crops and Products, vol. 29, 2009, pp. 371-376.
Parikh, D.V. et al., "Antimicrobial Silver/Sodium Carboxymethyl Cotton Dressings for Burn Wounds", Textile Research Journal, vol. 75, (2), 2005, pp. 134-138.
Liu, S. et al., "Durable and Regenerable Biocidal Polymers: Acyclic N-Halamine Cotton Cellulose", Ind. Eng. Chem. Res., vol. 45, 2006, pp. 6477-6482.
Son, Y-A et al., "Imparting Durable Antimicrobial Properties to Cotton Fabrics Using Quaternary Ammonium Salts Through 4-aminobenzenesulfonic Acid-Chloro-Triazine Adduct", European Polymer Journal, vol. 42, 2006, pp. 3059-3067.
Dubas, S.T. et al."Layer-by-Layer Deposition of Anticrobial Silver Nanoparticles on Textile Fibers", Colloids and Surfaces A: Physicochem. Eng. Aspects, vol. 289, 2006, pp. 105-109.
El-tahlawy, K.F. et al., "The Antimicrobial Activity of Cotton Fabrics Treated with Different Crosslinking Agents and Chitosan", Carbohydrate Polymers, vol. 60, 2005, pp. 421-430.
Sun, Y. et al., "Preparation and Physical and Antimicrobial Properties of A Cellulose-Supported Chloromelamine Derivative", Ind. Eng. Chem. Res., vol. 44, 2005, pp. 7916-7920.
American Association of Textile Chemists and Colorists, "AATCC Test Method 124, 2006 Appearance of Fabrics after Repeated Home Laundering", Developed in 1967 by AATCC Committee RA61 http://www.aatcc.org/Technical/Test_Methods/scopes/tm124.cfm.
American Association of Textile Chemists and Colorists, "AATCC Test Method 100-2004 Antibacterial Finishes on Textile Materials: Assessment of", Developed in 1961 by AATCC Committee RA31 http://www.aatcc.org/Technical/Test_Methods/scopes/tm100.cfm.
Chun, T.W. et al.,"Effects of Conventional Cotton Storage on Dust Generation Potential, Bacterial Survival, and Endotoxin Content of Lint and Dust", Ann. Agric. Environ. Med., vol. 3, 1996, pp. 19-25.

* cited by examiner

*Primary Examiner*—Lorna M Douyon
*Assistant Examiner*—Amina Khan
(74) *Attorney, Agent, or Firm*—John D. Fado; G. Byron Stover

(57) ABSTRACT

A method to bind compounds (e.g., antibiotics) to natural or synthetic yarn or fabric, involving reacting the compounds with cyanuric chloride, a hydroxide base (e.g., NaOH), and deionized water to form reactive compounds; forming a dyebath composed of the reactive compounds, at least one nonioinic, cationic or anionic surfactant, salt (e.g., sodium sulfate), deionized water, and natural or synthetic yarn or fabric; heating the dyebath (generally for about 1 to about 100 minutes at a temperature of about 25° to about 100° C.); adding a hydroxide base (e.g., NaOH) to the dyebath and heating (generally for about 1 to about 100 at a temperature of about 80° to about 100° C.); rinsing the natural or synthetic yarn or fabric; placing the natural or synthetic yarn or fabric in deionized water and heating (generally for about 1 to about 100 minutes at a temperature of about 25° to about 100° C.); rinsing the natural or synthetic yarn or fabric; and drying the natural or synthetic yarn or fabric. Also natural or synthetic yarn or fabric bound to antibiotics prepared by the method are disclosed herein.

6 Claims, No Drawings

METHOD FOR BINDING COMPOUNDS TO TEXTILES

REFERENCE TO RELATED APPLICATION

This application claims the benefit of U.S. Provisional Application No. 60/990,720, filed 28 Nov. 2007, which is incorporated herein by reference in its entirety.

BACKGROUND OF THE INVENTION

The present invention relates to a method to bind compounds (e.g., antibiotics) to natural or synthetic yarn or fabric, involving reacting the compounds with cyanuric chloride, a hydroxide base (e.g., NaOH), and deionized water to form reactive compounds; forming a dyebath composed of the reactive compounds, at least one nonioinic, cationic or anionic surfactant, salt (e.g., sodium sulfate), deionized water, and natural or synthetic yarn or fabric; heating the dyebath (generally for about 1 to about 100 minutes at a temperature of about 25° to about 100° C.); adding a hydroxide base (e.g., NaOH) to the dyebath and heating (generally for about 1 to about 100 at a temperature of about 80° to about 100° C.); rinsing the natural or synthetic yarn or fabric; placing the natural or synthetic yarn or fabric in deionized water and heating (generally for about 1 to about 100 minutes at a temperature of about 25° to about 100° C.); rinsing the natural or synthetic yarn or fabric, and drying the natural or synthetic yarn or fabric. The present invention also relates to natural or synthetic yarn or fabric bound to antibiotics prepared by the method disclosed herein.

The concept of antibacterial finishing of textiles appeared in 1941 in response to a need to protect the apparel of military personnel from hot and humid environmental conditions in the South Pacific Theater which were ideal for the growth of organisms on natural fiber substrates. More recently, an awareness of general sanitation, contact disease transmission, and personal protection have led to the development of antibacterial fibers to protect wearers against the spread of microorganisms (e.g., bacteria) and diseases rather than just to protect the quality and durability of the textile material. Most of these approaches entail the attachment of a biocidal or bacteriostatic agent to the fabric surface by a variety of mechanisms. These include the layer deposition of silver nanoparticles onto fabric structures, graft polymerization of N-halamide monomers onto cellulosic substrates, placement of quaternary ammonium salts onto cotton fabrics using a covalently bound adduct, covalent attachment of a chloromelamine derivative, and the attachment of chitosan to cotton fabric via cross-linking agents (Dubas, S. T., et al., Physicochem. Eng. Aspects, 289:105-109 (2006); Liu, S., and G. Sun, Ind. Eng. Chem. Res., 45:6477-6482 (2006); Son, Y. A., et al., European Polymer Journal, 42: 3059-3067 (2006); Sun, Y., et al., Ind. Eng. Chem. Res. 44:7916-7920 (2005); El-talawy, K. F., et al., Carbohydrate Polymers 60(4): 421-430 (2005)). However the problem exists of degradation of these agents upon washing.

We have found that antimicrobial (e.g., antibacterial) drugs can be directly attached to fabric or yarn (e.g., cotton) which does not exhibit degradation upon washing treatments.

SUMMARY OF THE INVENTION

In accordance with the present invention there is provided a method to bind compounds (e.g., antibiotics) to natural or synthetic yarn or fabric, involving reacting the compounds with cyanuric chloride, a hydroxide base (e.g., NaOH), and deionized water to form reactive compounds; forming a dyebath composed of the reactive compounds, at least one nonionic, cationic or anionic surfactant, a salt (e.g., sodium sulfate), deionized water, and natural or synthetic yarn or fabric; heating the dyebath (generally for about 1 to about 100 minutes at a temperature of about 25° to about 100° C.); adding a hydroxide base (e.g., NaOH) to the dyebath and heating (generally for about 1 to about 100 minutes at a temperature of about 80° to about 100° C.); rinsing the natural or synthetic yarn or fabric, placing the natural or synthetic yarn or fabric in deionized water and heating (generally for about 1 to about 100 minutes at a temperature of about 25° to about 100° C.), rinsing the natural or synthetic yarn or fabric, and drying the natural or synthetic yarn or fabric.

Also in accordance with the present invention is natural or synthetic yarn or fabric bound to compounds (e.g., antibiotics), prepared by the method disclosed herein.

DETAILED DESCRIPTION OF THE INVENTION

The present invention relates to a method to bind compounds (e.g., antibiotics) to natural or synthetic yarn or fabric, involving reacting the compounds with cyanuric chloride, a hydroxide base (e.g., NaOH), and deionized water to form reactive compounds; forming a dyebath composed of the reactive compounds, at least one nonionic (preferred), cationic or anionic surfactant, a salt (e.g., sodium sulfate), deionized water, and natural or synthetic yarn or fabric; heating the dyebath generally for about 1 to about 100 minutes (e.g., 1-100 minutes; preferably for about 20 to about 40 minutes (e.g., 20-40 minutes), more preferably for about 25 to about 35 minutes (e.g., 25-35 minutes)) at a temperature generally of about 25° to about 100° C. (e.g., 25°-100° C.; preferably about 50° to about 70° C. (e.g., 50°-70° C.), more preferably about 59° to about 61° C. (e.g., 59°-61° C.)); adding a hydroxide base (e.g., NaOH) to the dyebath and heating generally for about 1 to about 100 minutes (e.g., 1-100 minutes; preferably for about 25 to about 35 minutes (e.g., 25-35 minutes), more preferably for about 29 to about 31 minutes (e.g., 29-31 minutes)) at a temperature generally of about 80° to about 100° C. (e.g., 80°-100° C.; preferably about 80° to about 90° C. (e.g., 80°-90° C.), more preferably about 80° to about 85° C. (e.g., 80°-85° C.)); rinsing the natural or synthetic yarn or fabric; placing the natural or synthetic yarn or fabric in deionized water and heating generally for about 1 to about 100 minutes (e.g., 1-100 minutes; preferably about 10 to about 30 minutes (e.g., 10-30 minutes), more preferably about 10 to about 12 minutes (e.g., 10-12 minutes)) at a temperature generally of about 25° to about 100° C. (e.g., 25°-100° C.; preferably about 70° to about 100° C. (e.g., 70°-100° C.), more preferably about 75° to about 85° C. (e.g., 75°-85° C.)); rinsing the natural or synthetic yarn or fabric; and drying the natural or synthetic yarn or fabric. The present invention also relates to natural or synthetic yarn or fabric bound to antibiotics prepared by the method disclosed herein.

Generally about 0.8 to about 1.2 parts (e.g., 0.8-1.2 parts; preferably about 0.9 to about 1.1 parts (e.g., 0.9-1.1 parts), more preferably about 0.99 to about 1.01 parts (e.g., 0.99-1.01 parts), where parts are measured as any multiple of moles) of the compound to be bound to the textile is suspended in deionized water (generally above 0° C. to <5° C.) and reacted generally with about 1.6 to about 2.4 parts cyanuric chloride (e.g., 1.6-2.4 parts; preferably about 1.8 to about 2.2 parts (e.g., 1.8-2.2 parts), more preferably about 1.98 to about 2.02 parts (e.g., 1.98-2.02 parts)) and generally about 1.6 to about 2.4 parts NaOH (e.g., 1.6-2.4 parts; preferably about 1.8 to about 2.2 (e.g., 1.8-2.2 parts), more preferably about 1.98 to about 2.02 parts (e.g., 1.98-2.02 parts)) to form a reactive compound; any other hydroxide base may be used in place of NaOH. A dyebath is prepared by adding generally about 0.8 to about 1.2 parts of the reactive compound (e.g., 0.8-1.2 parts; preferably about 0.9 to about 1.1 parts (e.g., 0.9-1.1 parts), more preferably about 0.99 to about 1.01 parts (e.g., 0.99-1.01 parts)), generally about 0.0001 to about 1.0 of a nonioinic, cationic or anionic surfactant (e.g., 0.0001-1.0 parts; preferably about 0.001 to about 0.1 parts (e.g., 0.001-0.1 parts), more preferably about 0.03 to about 0.05 parts (e.g., 0.03-0.05 parts)), and generally about 0.1 to about 100 parts sodium sulfate or other salt (e.g., 0.1-100 parts; preferably about 1 to about 50 (e.g., 1-50 parts), more preferably about 19 to about 21 parts (e.g., 19-21 parts)) to water. The dyebath is heated generally at about 25° to about 100° C. (e.g., 25°-100° C.; preferably about 50° to about 70° C. (e.g., 50°-70° C.), more preferably about 59° to about 61° C. (e.g., 59°-61° C.)) and the fabric is submerged in the dyebath generally for about 1 to about 100 minutes (e.g., 1-100 minutes; preferably about 20 to about 40 minutes (e.g., 20-40 minutes), more preferably about 25 to about 35 minutes (e.g., 25-35 minutes)), then generally about 1 to about 30 parts NaOH (e.g., 1-30 parts; preferably about 10 to about 20 parts (e.g., 10-20 parts), more preferably about 14 to about 16 parts (e.g., 14-16 parts)) dissolved in water is added and the temperature raised to generally about 80° to about 100° C. (e.g., 80°-100° C.; preferably about 80° to about 90° C. (e.g., 80°-90° C.), more preferably about 80° to about 85° C. (e.g., 80°-85° C.)) and the fabrics heated generally for another about 1 to about 100 minutes (e.g., 1-100 minutes; preferably about 25 to about 35 minutes (e.g., 25-35 minutes), more preferably about 29 to about 31 minutes (e.g., 29-31 minutes)). The fabric is then rinsed in deionized water and then heated generally for about 1 to about 100 minutes (e.g., 1-100 minutes; preferably about 10 to about 30 (e.g., 10-30 minutes), more preferably about 10 to about 12 minutes (e.g., 10-12 minutes)) at a temperature generally of about 25° C. to about 100° C. (e.g., 25°-100° C.; preferably about 70° to about 100° C. (e.g., 70°-100° C.), more preferably about 75° to about 85° C. (e.g., 75°-85° C.)) in deionized water, then rinsed and kept in an oven (e.g., convection) at a temperature generally of about 20° to about 130° C. (e.g., 20°-130° C.; preferably about 60° to about 110° C. (e.g., 60°-110° C.), more preferably about 100° to about 105° C. (e.g., 100°-105° C.)) until dried.

For the purpose of this application an antimicrobial agent is any substance that kills or prevents the growth of a microorganism, and includes antibiotics, antifungal, antiviral, and antialgal agents. The antimicrobial agent of such a fabric should not be absorbed by the skin or other tissue with which it comes into contact so that relatively toxic agents may be successfully used topically. That is to say, the antimicrobial agent should be strongly bound to the fabric and remain so in use, i.e., have no substantial likelihood of migration from the fabric itself. A second desirable property is that the bound antimicrobial retain a substantial portion of the activity it exhibits in its unbound state. Furthermore, such antimicrobial activity and strong binding to the fabric should be retained over long periods of time so that such a fabric may be readily stored. Generally any compound (e.g., antibiotic) with an available amine group, such as trimethoprim and sulfamethoxazole, can be utilized in the present invention; other examples include sulfonamide drugs such as acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfasalazine, sultiame, sumatriptan, xipamide, zonisamide.

The claimed method is suitable for use with a broad variety of common woven or nonwoven fabrics. The underlying fabrics or fibers are subject to enormous variation. One desirable class of fabrics consists of cellulosics, as exemplified by cotton, linen, rayon, and cellulose acetate, and in many respects the cellulosic fibers, and especially cotton, are preferred in the practice of this invention. Other fabrics which may be used include silk, wool, and synthetics such as polyamides, polyesters, acrylics and modacrylics, polyolefins such as polypropylene, polyvinyl chloride, poly(vinylidene chloride), polyvinyl alcohol), poly(hydroxyacetic acid ester), polyurethanes, polytetrafluoroethylene, and copolymers of the above, phenolic type fibers (phenol-formaldehyde condensates), and polybenzimidazole fibers. See, e.g., Kirk-Othmer, Encyclopedia of Chemical Technology, Third Edition, Vol. 10, J. Wiley & Sons, Inc., 1980 (especially pp. 148, 181).

The cellulose-containing material may be any of the following: (a) fibers of cotton gauze (e.g., stretch cotton gauze), or cotton/polyolefin or cotton/polyester blends; (b) cellulose-containing impregnates including pine mesh gauze, paraffin and lanolin-coated gauze, polyethylene-coated gauze, knitted viscose, rayon, and cellulose blends of nylon and polyester; (c) cellulose-containing films, including those of a semipermeable or a semiocclusive nature such as polyurethane copolymers, acrylamides, acrylates, paraffin, polysaccharides, cellophane; (d) cellulose-containing hydrogels such as agar, starch or propylene glycol, which typically contain about 80% to about 90% water and are conventionally formulated as sheets, powders, pastes and gels in conjunction with crosslinked polymers such as polyethylene oxide, polyvinyl pyrollidone, acrylamide, propylene glycol.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Test Fabric: The fabric was supplied by Cotton Inc. (Cary, N.C.) from a commercial producer. The fabric was a white 100% cotton tight-weave denim-like fabric, weighing approximately 271.3 g/m$^2$, which had been commercially scoured and bleached. The fabric was cut into large squares, approximately 12.8 cm×12.8 cm, before being treated. After treatment, the large squares were ironed to remove wrinkles, cut into swatches of 18.1 cm$^2$ squares, 4.25 cm on a side, and sterilized in an autoclave using a drying cycle prior to the antibacterial assay.

Synthesis of Reactive Trimethoprim and Sulfamethoxazole to Covalently Bond With the Cotton Fabric:

Synthesis of 2,4-bis(2,4-dichloro-6-amino-s-triazino)-5-(3,4,5-trimethoxybenzyl)pyrimidine was accomplished by first suspending 5.80 g (0.02 mole) trimethoprim (2,4-diamino-5-3,4,5-trimethoxybenzyl pyrimidine; Sigma Chemical Co., St. Louis, Mo.) in 20 ml deionized water in an ice bath at 5° C. To this suspension was added 7.36 g (0.04 mole) cyanuric chloride (2,4,6-trichloro-1,3,5-triazine; Aldrich Chemical Co., St. Louis, Mo.). The suspension was maintained at 5° C. during the dropwise addition of 40-ml 1.0 N NaOH (0.04 mole).

Synthesis of 4-(2,4-dichloro-6-amino-s-triazino)-N-(5-methyl-3-isoxazolyl)benzenesulfonamide was accomplished by first suspending 7.59 g (0.03 mole) sulfamethoxazole (4-amino-N-(5-methyl-3-isoxazolyl)benzenesulfonamide; Sigma Chemical Co., St. Louis, Mo.) in 20 ml deionized water in an ice bath at 5° C. To this suspension was added 5.52 g (0.03 mole) cyanuric chloride. The suspension was maintained at 5° C. during the dropwise addition of 30-ml 1 N NaOH (0.03 mole).

Bonding the reactive antibiotic to cotton fabric: An exhaust dyeing method was used to bind the reactive antibiotic to the cotton fabric. First, a dyebath was prepared by the addition of 0.5 ml of Triton-X, 75 g of sodium sulfate, and 6.5 g of the reactive antibiotic (or 3.25 g of each of the two reactive antibiotics) to 1.2 L of deionized water. Three 20-g squares of the cotton fabric were submerged in the dyebath and the dyebath heated to 60° C. After 30 minutes of incubation, 12 g NaOH which had been dissolved in 100 ml of deionized water was added. The temperature was then raised to 80° C. and the fabrics heated for another 30 minutes. The fabric was then rinsed in deionized water and then heated for 10 minutes at 80° C. in deionized water, then rinsed and kept in a convection oven at 105° C. until dried.

Assay for antibacterial properties: The assay used for measuring antibacterial properties was based on the "AATCC Test Method 100-1999, Antibacterial Finishes on Textile Materials: Assessment of" (Anonymous, 1999a, AATCC Test Method 100-1999, Antibacterial Finishes on Textile Materials: Assessment of, pages 147-149, In: AATCC Technical Manual, Vol. 75, 2000 Technical Manual of the American Association of Textile Chemists and Colorists, 1999, AATCC, Triangle Park, N.C.); the assay has been described previously by Chun, D. T. W., et al. (Modification, Use of, and Description of AATCC Test Method 100-1999 to Test For Antibacterial Properties Of Denim Made from Flax Fabric, pages 2050-2050h, In: Proc. Beltwide Cotton Conf., San Antonio, Tex., 3-6 Jan. 2006, Natl. Cotton Counc. Am., Memphis, Tenn.; http://www.cotton.org/beltwide/proceedings/2006/pdfs/2050-2050.pdf). It was found that the population densities after incubation often remained the same or increased even with the controls, so the densities of the zero time of incubation for the controls and treatments were not determined. Test and control swatches were inoculated with challenge bacteria and after a period of incubation, the bacteria were eluted from the swatches with known volumes of extraction solution. Then the numbers of viable bacteria present in the extraction solutions were determined and the densities of the populations compared.

Two bacterial species were used: *Staphylococcus aureus*, American Type Culture Collection No. 6538 (a Gram-positive organism), and *Klebsiella pneumoniae*, American Type Culture Collection No. 4352 (a Gram-negative organism). Stock cultures were maintained on Difco Brain Heart Infusion Agar slants (Difco Brain Heart Infusion Agar, Man #237500). The stock cultures were transferred once every three to four weeks by incubating a freshly inoculated slant at 37°±2° C. for two days before storing at 5°±1° C.

For each assay, the challenge bacteria were incubated in either a trypticase soy broth (TSB, BBL® No. 11768 Trypticase Soy Broth) or on trypticase soy agar slants (TSA, BBL® No. 11768 Trypticase Soy Broth, and 2.0% agar) at 37°±2° C. for 1-3 days before being used to inoculate broth (TSB) cultures for testing. The inoculated broth cultures were incubated in a shake incubator (37°±2° C. and 300 rpm) for 24 hr. At the end of incubation, the broth cultures were placed in an ice bath and held until chilled.

To get a standardized density of bacteria for inoculation, the chilled cultures were diluted with TSB to a pre-determined turbidity to provide approximately $2\times10^9$ CFU/ml or $2\times10^8$ CFU/ml. The turbidity was measured at 500 nm on a Beckman DU-7 Spectrophotometer (Beckman Instruments, Inc., Irvine Calif.) using chilled TSB from the same batch as the cultures were grown in to zero the instrument. Then the diluted broth cultures were serially diluted with chilled diluent without Tween-80 or gelatin (Chun, D. T. W., and H. H. Perkins, Jr., Ann. Agric. Environ. Med., 3:19-25 (1996)) for a final approximate bacterial density of $1\text{-}2\times10^5$ CFU/ml; from trial and error, a fudge factor was included where 0.5 ml of the initial broth culture was added early in the dilution series to compensate for the observed loss from the expected population starting density to the actual starting density used in the assays. The bacterial suspensions were kept in an ice bath. A magnetic stirring bar and stirring plate was used to keep the bacteria suspended during inoculation.

For each replicate sample, 1.0±0.1 mL of inoculum was dispersed as droplets over the three swatches using a Rainin EDP-Plus Electronic Pipette (RAININ Instrument Co., Inc., Woburn, Mass.). The swatches were inoculated while in pre-sterilized 237 ml (half pint) canning jars (Mason or Kerr Brand, locally obtained). The bands and lids of the canning jars were screwed on the jars to prevent evaporation. After all the samples had been inoculated, the jars were incubated at 37°±2° C. for 24 hours before being assayed for bacterial population density.

The bacterial population density was determined by first extraction of the bacteria from the fabric by adding 100 mL of diluent to each jar and shaking the jars on a tabletop shaker for one minute. Then aliquots were removed and plated directly onto. Petri dishes or further diluted before being plated. The pour plate method (Chun and Perkins, 1996) was used to determine the bacterial density. No antibiotics were used and incubation was at 37°±2° C. for at least 24 hours before the plates were counted. Experimental Design and Statistical Analysis: Four main fabric treatments were considered: (A) a control fabric which had not been chemically altered; (B) fabric which had trimethoprim covalently bonded to it; (C) fabric which had sulfamethoxazole covalently bonded to it; and (D) fabric which had both trimethoprim and sulfamethoxazole covalently bonded to it. Before assaying these four treatments, a trial run using just the control and trimethoprim treated fabric was conducted to see if covalently bonding the antibiotic would take and if the attachment of the antibiotic would persist through multiple washings. The fabric washing was done by Cotton Inc. which was based on the AATCC Test Method 124-1996 (Anonymous, AATCC Test Method 124-1996, Appearance of Fabrics after Repeated Home Laundering, pages 205-208, In: AATCC Technical Manual, Vol. 75, 2000 Technical Manual of the American Association of Textile Chemists and Colorists, 1999, AATCC, Triangle Park, N.C.) laundering procedure: normal/cotton sturdy cycle, 1.81 kg (4 lb) load, warm water temperature, and AATCC detergent without optical brightener. The treated and control samples were washed three and ten times. For this trial run, only the *K. pneumoniae* challenge results will be presented.

In the antibacterial assays, the bacterial inoculum was dispersed as droplets over three swatches per replicate sample. Three swatches were used instead of four since the fabric was highly absorbent and three replicate samples were used for each treatment. Often the observations of replicate tests were combined and used for statistical analysis. Replicate tests were done and the observations were combined and used for statistical analysis. A log 10(CFU+1), where CFU=microbial population as colony forming units, transformation was used for the analysis dealing with the microbial data. Data were analyzed with release 8.00 of SAS (SAS, Statistical Analysis System; SAS system for Windows NT, SAS Institute Inc., Cary, N.C.) for Duncan mean comparisons. Microsoft® Office Excel 2003 (Microsoft Corporation, USA) was used to randomize treatment assignments, to enter and store data, to sort data and prepare for SAS analysis, to transform data, to summarize and tabulate results, to obtain simple treatment statistics (means, standard deviations, regressions, etc.), and to perform other spreadsheet functions. Data were analyzed with release 8.00 of SAS (SAS, Statistical Analysis System; SAS system for Windows NT, SAS Institute Inc., Cary, N.C.) for Duncan mean comparisons when the analysis of variance analysis yielded significant "F-values" to indicate a high degree of difference of the variable to the variation. Microsoft® Office Excel 2003 (Microsoft Corporation, USA) was used to randomize treatment assignments, to enter and store data, to sort data and prepare for SAS analysis, to transform data, to summarize and tabulate results, to obtain simple treatment statistics (means, standard deviations, regressions, t-test comparison, etc.), and to perform other spreadsheet functions.

Results and Discussion: Initial testing was performed to first determine if the reactive antibiotics would covalently bond to the cotton fabric and if so doing would impart antibiotic properties to the fabric. A single pilot test was done with trimethoprim using both the $S.$ $aureus$ and $K.$ $pneumoniae$ challenge bacteria. With the $S.$ $aureus$ challenge, the control swatches averaged 6.291 (Log 10(CFU+1)) while the trimethoprim-swatches averaged 5.101 (Log 10(CFU+1)). With the $K.$ $pneumoniae$ challenge, the control swatches averaged 7.743 (Log 10(CFU+1)) while the trimethoprim-swatches averaged 4.333(Log 10(CFU+1)). The differences between the means of the control and the trimethoprim-treated swatches were highly significant using t-test analysis for the $S.$ $aureus$ and $K.$ $pneumoniae$ challenge, $P=0.011$ and $P<0.001$, respectively. This strongly suggested to us that the antibiotic was surprisingly bound to the cotton fabric and that the antibacterial effect of the trimethoprim was not sacrificed.

This first batch of treated fabric was next repeatedly washed to determine if the antibiotic binding to the fabric would be durable through normal washing. The large swatches of treated and untreated cotton fabric were sent out to Cotton Inc. to be washed three and ten times. When these large swatches were returned, they were cut into smaller swatches, sterilized and then assayed for antibacterial properties. Both the $S.$ $aureus$ and $K.$ $pneumoniae$ challenge were used, but only the $K.$ $pneumoniae$ challenge results will be reported. The $S.$ $aureus$ challenge results showed that the difference between the unwashed control and the trimethoprim treated swatches were significantly different as before, 5.758 and 4.202 (Log 10(CFU+1)), respectively. The observations from two tests using the $K.$ $pneumoniae$ challenge (Table 1) were combined and analyzed. The three controls all showed the same high bacterial density of about 7.0 (Log 10(CFU+1)) and the averages of the controls were not significantly different from one another which suggested no untold affect by the washing procedure that would on its own affect the bacterial density. But the treated fabric, both unwashed and washed, were significantly lower with an average density of about 3.5 (Log 10(CFU 1)), and the averages were not significantly different whether the treated fabric were unwashed or washed three or ten times. These results indicated that the antibacterial property imparted by binding trimethoprim to cotton was surprisingly durable and retained at least through ten washes.

Additional fabric was treated with trimethoprim. In addition, fabric was also treated with sulfamethoxazole and a 1:1 mixture of trimethoprim and sulfamethoxazole (both at half the strength of when used alone). The observations from three separate antibacterial assays were combined and analyzed (Table 2). The results indicated that both trimethoprim and sulfamethoxazole, individually or together, surprisingly depressed the bacterial density significantly after the 24-hr incubation in both the $K.$ $pneumonia$ and $S.$ $aureus$ challenge. Binding sulfamethoxazole to fabric produced a weaker effect than trimethoprim alone or when both trimethoprim and sulfamethoxazole were attached to the fabric. But the trimethoprim treated fabric and the trimethoprim and sulfamethoxazole treated fabric were not significantly different; that is, while sulfamethoxazole treated fabric was bacteriostatic compared to the controls, when used in combination with trimethoprim, its added effect to the effect of trimethoprim alone was not significantly different than using just trimethoprim alone. However, the total amount of trimethoprim and sulfamethoxazole in the 1:1 mixture treatment was half the amount used in the tests of the compounds tested individually. This argued for the possibility that the two compounds may have had a synergistic effect to account for the low bacterial density comparable to trimethoprim used alone or the amount of the individually applied antibiotic was in excess to what is needed to effectively lower the bacterial density to this level. This also suggested that the reactive trimethoprim may have been preferentially attached to the cotton fabric and that at even half the dose this alone could account for the lower bacterial density when combined with sulfamethoxazole.

Inasmuch as trimethoprim and sulfamethoxazole were both easily prepared to act as reactive dyes and that many, if not most, of other commonly known antibiotic compounds have the same or similar reactive sites, it is expected that many other antibiotics may be used in a similar manner. This opens up the opportunity to create designer or tailored antimicrobial fabric or yarn using the reactive dye method described herein to attach antibacterial compounds to, for example, cotton. For example, one area where this approach may prove to be of value would be to attach scarce antibacterial drugs to dressings to act as barriers to specific drug resistant bacteria to help prevent or reduce infection and its spread. In addition, the reactive dye mechanism will potentially prevent an alteration in the hand and moisture migration properties of the treated fabric, which is one drawback of using a polymer grafted type mechanism.

All of the references cited herein, including U.S. Patents, are incorporated by reference in their entirety. Also incorporated by reference in their entirety are the following references: Parikh, D. V., et al., Textile Res. J., 75:134-138 (2005); U.S. Pat. No. 4,810,567.

Thus, in view of the above, the present invention concerns (in part) the following:

A method to (covalently) bind compounds to natural or synthetic yarn or fabric, comprising or consisting essentially of or consisting of (A) reacting said compounds with cyanuric chloride, a hydroxide base, and deionized water to form reactive compounds; (B) forming a dyebath composed of (i) said reactive compounds, (ii) at least one surfactant, (iii) a salt, (iv) deionized water, and (v) natural or synthetic yarn or fabric; (C) heating said dyebath for about 1 to about 100 minutes at a temperature of about 25° to about 100° C.; (D) adding a hydroxide base to said dyebath and heating for about 1 to about 100 minutes at a temperature of about 80° to about 100°

C.; (E) rinsing said natural or synthetic yarn or fabric; (F) placing said natural or synthetic yarn or fabric in deionized water and heating for about 1 to about 100 minutes at a temperature of about 25° to about 100° C.; (F) rinsing said natural or synthetic yarn or fabric; and (H) drying said natural or synthetic yarn or fabric.

The above method, wherein said surfactant is selected from the group consisting of nonioinic surfactant, cationic surfactant, anionic surfactant, and mixtures thereof.

The above method, wherein said surfactant is nonioinic surfactant. The above method, wherein said hydroxide base is NaOH.

The above method, wherein said salt is sodium sulfate.

The above method, wherein said compounds are antibiotics (e.g., trimethoprim, sulfamethoxazole, acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfasalazine, sultiame, sumatriptan, xipamide, zonisamide).

Natural or synthetic yarn or fabric (covalently) bound to antibiotics, prepared by the above method.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Bacterial density, $Log_{10}(CFU + 1)$, after 24-hr incubation on cotton fabric treated with trimethoprim after 0, 3 and 10 washes.

| Treatment | *Klebsiella pneumoniae* density, $Log_{10}(CFU + 1)^z$ |
| --- | --- |
| Control, Unwashed | $7.265^A$ |
| Control, Washed 3 Times | $6.847^A$ |
| Control, Washed 10 Times | $6.774^A$ |
| Treated with Trimethoprim, Unwashed | $3.442^B$ |
| Treated with Trimethoprim, Washed 3 Times | $3.310^B$ |
| Treated with Trimethoprim, Washed 10 times | $3.645^B$ |

$^z$Mean separation within column by Duncan's multiple range test, 5% level. Means with the same letter are not significantly different.

TABLE 2

Bacterial density, $Log_{10}(CFU + 1)$, after 24-hr incubation on cotton fabric treated with either trimethoprim or sulfamethoxazole or both.

| Treatment | |
| --- | --- |
| | *Klebsiella pneumoniae* density, $Log_{10}(CFU + 1)^z$ |
| Control | $6.830^A$ |
| Treated with Trimethoprim | $2.793^{BC}$ |

TABLE 2-continued

Bacterial density, $Log_{10}(CFU + 1)$, after 24-hr incubation on cotton fabric treated with either trimethoprim or sulfamethoxazole or both.

| Treatment | |
| --- | --- |
| Treated with Sulfamethoxazole | $3.618^B$ |
| Treated with Trimethoprim and Sulfamethoxazole | $2.147^{BC}$ |
| | *Staphylococcus aureus* density, $Log_{10}(CFU + 1)^z$ |
| Control | $6.084^A$ |
| Treated with Trimethoprim | $3.794^C$ |
| Treated with Sulfamethoxazole | $4.407^B$ |
| Treated with Trimethoprim and Sulfamethoxazole | $3.773^C$ |

$^z$Mean separation within column by Duncan's multiple range test, 5% level. Means with the same letter are not significantly different.

We claim:

1. A method to bind compounds to natural or synthetic yarn or fabric wherein said compounds are selected from the group consisting of trimethoprim, sulfamethoxazole, acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfasalazine, sultiame, sumatriptan, xipamide, zonisamide, and mixtures thereof, comprising reacting said compounds with cyanuric chloride, a hydroxide base, and deionized water to form reactive compounds, forming a dyebath composed of said reactive compounds, at least one surfactant, a salt, deionized water, and natural or synthetic yarn or fabric, heating said dyebath for about 1 to about 100 minutes at a temperature of about 25° to about 100° C., adding a hydroxide base to said dyebath and heating for about 1 to about 100 minutes at a temperature of about 80° to about 100° C., rinsing said natural or synthetic yarn or fabric, placing said natural or synthetic yarn or fabric in deionized water and heating for about 1 to about 100 minutes at a temperature of about 25° to about 100° C., rinsing said natural or synthetic yarn or fabric, and drying said natural or synthetic yarn or fabric.

2. The method according to claim 1, wherein said surfactant is selected from the group consisting of nonioinic surfactant, cationic surfactant, anionic surfactant, and mixtures thereof.

3. The method according to claim 1, wherein said surfactant is a nonioinic surfactant.

4. The method according to claim 1, wherein said hydroxide base is NaOH.

5. The method according to claim 1, wherein said salt is sodium sulfate.

6. The method according to claim 1, wherein said compounds are selected from the group consisting of trimethoprim, sulfamethoxazole, and mixtures thereof.

* * * * *